(12) United States Patent
Choi (10) Patent No.: US 11,302,455 B2
(45) Date of Patent: Apr. 12, 2022

(54) ***DEINOCOCCUS RADIODURANS* HAVING GOLD NANOPARTICLE SYNTHESIS ABILITY, AND METHOD FOR REMOVING RADIOACTIVE IODINE BY USING SAME**

(71) Applicant: UNIVERSITY OF SEOUL INDUSTRY COOPERATION FOUNDATION, Seoul (KR)

(72) Inventor: Yong Jun Choi, Seoul (KR)

(73) Assignee: UNIVERSITY OF SEOUL INDUSTRY COOPERATION FOUNDATIO, Seoul (KR)

( * ) Notice: Subject to any disclaimer, the term of this patent is extended or adjusted under 35 U.S.C. 154(b) by 435 days.

(21) Appl. No.: 16/348,594

(22) PCT Filed: Oct. 19, 2017

(86) PCT No.: PCT/KR2017/011582
§ 371 (c)(1),
(2) Date: May 9, 2019

(87) PCT Pub. No.: WO2018/088712
PCT Pub. Date: May 17, 2018

(65) Prior Publication Data
US 2019/0355487 A1    Nov. 21, 2019

(30) Foreign Application Priority Data

Nov. 11, 2016 (KR) ........................ 10-2016-0150372

(51) Int. Cl.
*C12N 1/20* (2006.01)
*G21F 9/16* (2006.01)
(Continued)

(52) U.S. Cl.
CPC ................ *G21F 9/16* (2013.01); *C12N 1/20* (2013.01); *C12N 15/74* (2013.01); *C12N 1/205* (2021.05);
(Continued)

(58) Field of Classification Search
None
See application file for complete search history.

(56) References Cited

U.S. PATENT DOCUMENTS

2019/0355487 A1* 11/2019 Choi ...................... C12N 15/74

FOREIGN PATENT DOCUMENTS

WO    WO-0123526 A1 *  4/2001  ............. C12N 1/205

OTHER PUBLICATIONS

Chaturvedi, R. et al., "Cytosolic Espression of Synthetic Phytochelatin and Bacterial Metallothionein Genes in Deinococcus Radiodurans R1 for Enhanced Tolerance and Bioaccumulation of Cadmium", Biometals, Mar. 1, 2014, vol. 27, pp. 471-482.
(Continued)

*Primary Examiner* — Richard C Ekstrom
(74) *Attorney, Agent, or Firm* — Elmore Patent Law Group, P.C.; Joseph C. Zucchero; Carolyn S. Elmore (57) ABSTRACT

A method for removing iodine by using *Deinococcus radiodurans* having a gold nanoparticle synthesis ability is disclosed. More particularly, a method for removing radioactive iodine by adsorbing radioactive iodine onto gold nanoparticles synthesized in cells of *Deinococcus radiodurans* is disclosed. A recombinant microorganism having an enhanced radioactive iodine removal ability according to the present invention may selectively remove radioactive iodine present in various types of solutions at a high efficiency of 99% or higher, and thus may be very effective in
(Continued)

removing radioactive iodine generated in large-scale hospitals, industries, nuclear facility accidents, and the like.

10 Claims, 6 Drawing Sheets

Specification includes a Sequence Listing.

(51) Int. Cl.
  *C12N 15/74* (2006.01)
  *C12R 1/01* (2006.01)
(52) U.S. Cl.
  CPC ...... *C12N 2500/10* (2013.01); *C12R 2001/01* (2021.05)

(56) References Cited

OTHER PUBLICATIONS

Appukuttan, D. et al., "Engineering of Deinococcus Radiodurans R1 for Bioprecipitation of Uranium from Dilute Nuclear Waste", Applied and Environmental Microbiology, Oct. 20, 2006, vol. 72, No. 12, pp. 7873-7878.

Lange, C. C. et al., "Engineering a Recombinant Deinococcus Radiodurans for Organopollutant Degradation in Radioactive Mixed Waste Environments", Nature Biotechnology, Oct. 1998, vol. 16, pp. 929-933.

Li, J. et al., "Biosynthesis of Gold Nanoparticles by the Extreme Bacterium Deinococcus Radiodurans and an Evaluation of Their Antibacterial Properties", International Journal of Nanomedicine, Nov. 9, 2016, vol. 11, pp. 5931-5944.

Iravani, S., "Bacteria in Nanoparticle Synthesis: Current Status and Future Prospects", International Scholarly Research Notices, Oct. 29, 2014, vol. 2014, article No. 359316, pp. 1-18.

NCIB, GeneBank accession No. AF085230.1 (Jun. 22, 1999).

Choi, M. H. et al., "Gold-nanoparticle-immobilized Desalting Columns for Highly Efficient and Specific Removal of Radioactive Iodine in Aqueous Media", ACS Applied Material & Interfaces, Oct. 19, 2016, vol. 8, No. 43, pp. 29227-29231.

Yang, D. et al., "Capture of Radioactive Cesium and Iodide Ions from Water by Using Titanate Nanofibers and Nanotubes", Angew. Chem. Int. Ed., 2011, 50, 10594-10598.

Lefèvre, G. et al., "Immobilization of iodide on copper(I) sulfide minerals", Journal of Environmental Radioactivity, 70 (2003) 73-83.

Ismail, S.S., et al., "Cs, Trace and Toxic Elements Distribution in Austrian Mushrooms", J. Radioanal. Nucl. Chem., Letters, 200(4): 315-336 (1995).

Neumann, E., et al., "Gene transfer into mouse lyoma cells by electroporation in high electric fields", The EMBO Journal, 1(7): 841-845 (1982).

* cited by examiner

FIG. 1

>metallothionein_opti (225 bp)

ATGAACGATCAGCGCTGCGCCTGCACCCACTGCTCCTGCACCGTGGACGCCAACGCGCTCCAGCGCGACGGCAAAGCTTACTGTTGCGAAGCCTGCGCCAGCGGCCACCGCAAGGG
GGAACCCTGCCGGATGCAGGACTGCCACTGTGGCGAGAAGCCCGGCGAGAGCGCGGTGGACAACGCGCTGGACGAAACGTTCCCGGCGAGCGACCCGATCTCGCCCTGA

Information
    GC contents : 68.0 %
    Tandem repeat : Nothing
    Interspersed repeat :

| Size | Count | Start |
|---|---|---|
| 9 | 2 | 51,177 |
| 9 | 2 | 157,186 |
| 6 | 2 | 20,35 |

Invert repeat : Nothing
    Homo-Poly : Nothing
    Toxic : No

FIG. 2

>phytochelatin synthase 1_opti (1458 bp)

```
ATGGCTATGGCGAGTCTCTATCGGCGAAGTCTTCCGTCGCCTCCGGCCATCGACTTTAGTTCGGCTGAGGGCAAGTTGATCTTCAATGAGGCGCTTCAGAAAGGAACTATGGAGGG
ATTCTTTCGATTGATTTCGTACTTTCAGACTCAATCCGAGCCTGCGTATTGTGGCTTGGCTAGTCTCTCAGTGGTGTTGAACGCTCTTTCTATCGATCCTGGACGCAAGTGGAAGG
GGCCTTGGCGGTGGTTTGACGAATCGATGTTGGACTGCTGCGAGCCTCTGGAAGTAGTGAAGGAAAAGGGCATCTCATTTGGAAAAGTGGTGTGTTTGGCCCACTGCTCAGGAGCT
AAAGTCGAGGCCTTCCGCACGAGTCAATCGACCATTGACGATTTCCGCAAGTTTGTCGTCAAATGCACGAGTTCGGAGAATTGCCACATGATCTCAACTTACCACCGGAGTGTCTT
TAAGCAGACTGGGAATGGACACTTTTCACCTATTGGTGGCTACAATGCCGAACGCGATATGCCTTGATTCTTGATGTGGCGAGGTTCAAGTATCCCCTCACTGGGTCCCCTCA
AACTTCTTTGGGAGGCTATGGACAGTATTGATCAGTCAACCGGGAAACGTCGAGGGTTCATGCTCATCAGCCGGCCACACCGCGAACCCGGATTGCTCTATACTCTGAGCTGCAAG
GACGAAAGCTGGATCGAAATCGCCAAGTATTTGAAGGAGGACGTCCCTCGTCTTGTAAGTAGCCAGCACGTAGATAGCGTGGAGAAAATCATCTCAGTTGTGTTCAAATCACTTCC
CTCAAACTTCAACCAGTTCATCCGGTGGGTGGCTGAAATTCGTATTACCGAGGACTCAAACCAGAACCTCTCTGCCGAGGAGAAATCCCGACTGAAATTGAAGCAGTTGGTGCTGA
AGGAGGTGCACGAGACTGAACTGTTCAAGCACATCAATAAATTCCTCTCCACCGTGGGGTACGAAGACAGCCTGACGTACGCTGCTGCGAAGGCTTGCTGCCAAGGAGCTGAAATC
CTTTCCGGAAGCCCCTCGAAAGAGTTCTGCTGCCGGGAGACTTGCGTGAAATGCATCAAAGGCCCTGATGACAGCGAAGGCACAGTGGTGACGGGGGTTGTGGTGCGGGATGGCAA
TGAGCAAAAGGTCGACCTGCTGGTGCCTTCGACGCAAACTGAGTGCGAATGTGGTCCTGAAGCAACCTATCCGGCGGGAAACGACGTCTTCACTGCGCTTCTGTTGGCTCTTCCTC
CACAGACGTGGAGTGGGATCAAGGACCAAGCTCTTATGCATGAAATGAAGCAGCTGATTTCCATGGCTTCCCTCCCGACTCTCCTTCAAGAAGAGGTGTTGCATCTTCGGCGGCAA
CTCCAGCTGCTGAAACGATGCCAAGAGAACAAGGAAGAGGATGACCTCGCTGCTCCTGCGTACTGA
```

Information
GC contents : 52.0 %
Tandem repeat : Nothing
Interspersed repeat :

| Size | Count | Start |
|---|---|---|
| 12 | 2 | 575,611 |
| 9 | 2 | 267,1010 |
| 9 | 2 | 556,572 |
| 9 | 2 | 578,814 |
| 9 | 2 | 621,1235 |
| 9 | 2 | 728,926 |
| 8 | 2 | 3,984 |
| 8 | 2 | 157,1447 |
| 8 | 2 | 185,1127 |
| 8 | 2 | 186,318 |
| 8 | 2 | 365,413 |
| 8 | 2 | 412,935 |
| 8 | 2 | 808,1343 |

Invert repeat : Nothing
Homo-Poly : Nothing
Toxic : No

A     DC-R1 without Au       With Au

SEQUENCE LISTING

<160> NUMBER OF SEQ ID NOS: 8

<210> SEQ ID NO 1
<211> LENGTH: 225
<212> TYPE: DNA
<213> ORGANISM: Pseudomonas putida

<400> SEQUENCE: 1

```
atgaacgatc agcgctgcgc ctgcacccac tgctcctgca ccgtggacgc caacgcgctc      60
cagcgcgacg gcaaagctta ctgttgcgaa gcctgcgcca gcggccaccg caaggggaa      120 ccctgccgga tgcaggactg ccactgtggc gagaagcccg gcgagagcgc ggtggacaac      180
gcgctggacg aaacgttccc ggcgagcgac ccgatctcgc cctga                     225
```

<210> SEQ ID NO 2
<211> LENGTH: 1458
<212> TYPE: DNA
<213> ORGANISM: Arabidopsis thaliana

<400> SEQUENCE: 2

```
atggctatgg cgagtctcta tcggcgaagt cttccgtcgc ctccggccat cgactttagt      60
tcggctgagg gcaagttgat cttcaatgag gcgcttcaga aaggaactat ggagggattc     120
tttcgattga tttcgtactt tcagactcaa tccgagcctg cgtattgtgg cttggctagt     180
ctctcagtgg tgttgaacgc tctttctatc gatcctggac gcaagtggaa ggggccttgg     240
cggtggtttg acgaatcgat gttggactgc tgcgagcctc tggaagtagt gaaggaaaag     300
ggcatctcat ttggaaaagt ggtgtgtttg gcccactgct caggagctaa agtcgaggcc     360
ttccgcacga gtcaatcgac cattgacgat tccgcaagt tgtcgtcaa atgcacgagt       420 tcggagaatt gccacatgat ctcaacttac caccggagtg tctttaagca gactgggaat     480
ggacactttt cacctattgg tggctacaat gccgaacgcg atatggcctt gattcttgat     540
gtggcgaggt tcaagtatcc ccctcactgg gtccccctca aacttctttg ggaggctatg     600
gacagtattg atcagtcaac cgggaaacgt cgagggttca tgctcatcag ccggccacac     660
cgcgaacccg gattgctcta tactctgagc tgcaaggacg aaagctggat cgaaatcgcc     720
aagtatttga aggaggacgt ccctcgtctt gtaagtagcc agcacgtaga tagcgtggag     780
aaaatcatct cagttgtgtt caaatcactt ccctcaaact tcaaccagtt catccggtgg     840
gtggctgaaa ttcgtattac cgaggactca aaccagaacc tctctgccga ggagaaatcc     900
cgactgaaat tgaagcagtt ggtgctgaag gaggtgcacg agactgaact gttcaagcac     960
atcaataaat tcctctccac cgtggggtac gaagacagcc tgacgtacgc tgctgcgaag    1020
gcttgctgcc aaggagctga aatcctttcc ggaagcccct cgaaagagtt ctgctgccgg    1080
gagacttgcg tgaaatgcat caaaggccct gatgacagcg aaggcacagt ggtgacgggg    1140
gttgtggtgc gggatggcaa tgagcaaaag gtcgacctgc tggtgccttc gacgcaaact    1200
gagtgcgaat gtggtcctga agcaacctat ccggcgggaa acgacgtctt cactgcgctt    1260
ctgttggctc ttcctccaca gacgtggagt gggatcaagg accaagctct tatgcatgaa    1320
atgaagcagc tgatttccat ggcttccctc ccgactctcc ttcaagaaga ggtgttgcat    1380
cttcggcggc aactccagct gctgaaacga tgccaagaga acaaggaaga ggatgacctc    1440
gctgctcctg cgtactga                                                  1458

<210> SEQ ID NO 3
<211> LENGTH: 40
<212> TYPE: DNA
<213> ORGANISM: Artificial Sequence
<220> FEATURE:
<223> OTHER INFORMATION: GroMT_3

<400> SEQUENCE: 3
ggcggccgtt actagtggat atgaacgatc agcgctgcgc                            40

<210> SEQ ID NO 4
<211> LENGTH: 30
<212> TYPE: DNA
<213> ORGANISM: Artificial Sequence
<220> FEATURE:
<223> OTHER INFORMATION: GroMT_4

<400> SEQUENCE: 4
tattggatcc tcagggcgag atcgggtcgc                                       30

<210> SEQ ID NO 5
<211> LENGTH: 32
<212> TYPE: DNA
```

```
<213> ORGANISM: Artificial Sequence
<220> FEATURE:
<223> OTHER INFORMATION: GroMT_1

<400> SEQUENCE: 5
tattgcggcc gcttggaagc acgtattgtc gc                          32

<210> SEQ ID NO 6
<211> LENGTH: 40
<212> TYPE: DNA
<213> ORGANISM: Artificial Sequence
<220> FEATURE:
<223> OTHER INFORMATION: GroMT_2

<400> SEQUENCE: 6
gcgcagcgct gatcgttcat atccactagt aacggccgcc                  40

<210> SEQ ID NO 7
<211> LENGTH: 35
<212> TYPE: DNA
<213> ORGANISM: Artificial Sequence
<220> FEATURE:
<223> OTHER INFORMATION: AtPCR_F

<400> SEQUENCE: 7
gccgcgacta gtatggctat ggcgagtctc tatcg                       35

<210> SEQ ID NO 8
<211> LENGTH: 33
<212> TYPE: DNA
<213> ORGANISM: Artificial Sequence
<220> FEATURE:
<223> OTHER INFORMATION: AtPCR_R

<400> SEQUENCE: 8
tatatgcggc cgctcagtac gcaggagcag cga                         33
```

DEINOCOCCUS RADIODURANS HAVING GOLD NANOPARTICLE SYNTHESIS ABILITY, AND METHOD FOR REMOVING RADIOACTIVE IODINE BY USING SAME

TECHNICAL FIELD

The present invention relates to a method for removing iodine by using *Deinococcus radiodurans* having a gold nanoparticle synthesis ability, and more particularly, to a method for removing radioactive iodine by adsorbing radioactive iodine onto gold nanoparticles synthesized in cells of *Deinococcus radiodurans*.

BACKGROUND ART

Due to nuclear power plant accidents such as the nuclear power plant explosion accident in Fukushima, Japan in 2011, the Chernobyl accident, and the like, the possibility of radioactive iodine contamination continues to increase, and also in Korea, it was reported in 2011 that radioactive iodine was detected throughout the nation (Apr. 18, 2011, Kyunghyang Nawspaper). In addition, recent increases in the number of patients with thyroid cancer (300,000, USA, 2008) have led to a surge in the amount of iodine used for the treatment of thyroid cancer. According to Survey on the Status of Radiation/Radioactive Isotope Utilization (2013) conducted by the Korea Association for Radiation Application, in line with an increase in the number of patients with thyroid cancer, the demand for radioactive isotopes used in treating thyroid cancer has been increasing for several years, and among the radioactive isotopes, $I^{131}$ is the most widely used nuclide species.

When such radioactive iodine is absorbed into the human body in an uncontrollably large amount, problems such as the occurrence of cancer and abnormal hormone secretion, and the like may occur, and serious environmental pollution problems may occur, and thus it may be very important to effectively treat and remove radioactive iodine waste discharged into the environment.

Many methods for removing metal radioactive isotopes have been developed, but research on methods and apparatuses for selectively removing radioactive iodine has not been adequately conducted.

As a currently used representative technique for removing radioactive iodine, there is a method for removing radioactive iodine by adsorbing radioactive iodine in water using activated carbon (*J. Radioanal. Nucl. Chem.* 200: 351, 1995). However, this method requires the use of relatively bulky activated carbon, and consequently, new solid radioactive waste may be continuously generated and removal efficiency thereof is low. As another method, a technique for removing radioactive iodine by reacting radioactive iodine with silver to thereby induce precipitation of the radioactive iodine was utilized (*Angew. Chem., Int. Ed.* 50: 10594, 2011). However, silver has high affinity to other anions (e.g., chlorine ($Cl^-$)), and thus has poor radioactive iodine removal efficiency, and this method is known to require high costs, as compared to other methods. Also, a method for selectively removing radioactive iodine present in water by using ionic copper-containing bentonite has recently been developed (*J. Environ. Radioact.* 70: 73, 2003). However, this method also does not have high radioactive iodine removal efficiency, and a relatively long period of time is required to remove radioactive iodine.

Therefore, the inventors of the present invention have made intensive efforts to develop a method capable of economically, specifically, and efficiently removing iodine within a short time period, and as a result, they confirmed that *Deinococcus radiodurans*, which is capable of synthesizing gold nanoparticles in cells thereof, specifically and efficiently removed radioactive iodine within a short time period by strongly adsorbing the radioactive iodine into the cells, and thus completed the present invention.

DISCLOSURE

Technical Problem

Therefore, the present invention has been made in view of the above problems, and it is an object of the present invention to provide a recombinant microorganism having an enhanced radioactive iodine removal ability in which a polynucleotide represented by a nucleotide sequence of SEQ ID NO: 1 or 2 is introduced into *Deinococcus radiodurans* ATCC13939.

It is another object of the present invention to provide a method of preparing gold nanoparticles by using the recombinant microorganism, and a method for removing radioactive iodine by using the recombinant microorganism.

Technical Solution

In accordance with the present invention, the above and other objects can be accomplished by the provision of a recombinant microorganism having an enhanced radioactive iodine removal ability in which a polynucleotide represented by a nucleotide sequence of SEQ ID NO: 1 is introduced into *Deinococcus radiodurans* ATCC13939.

In accordance with an aspect of the present invention, the above and other objects can be accomplished by the provision of a recombinant microorganism having an enhanced radioactive iodine removal ability in which a polynucleotide represented by a nucleotide sequence of SEQ ID NO: 2 is introduced into *Deinococcus radiodurans* ATCC13939.

In accordance with another aspect of the present invention, there is provided a method of preparing gold nanoparticles by using a recombinant microorganism having an enhanced radioactive iodine removal ability, the method including culturing the recombinant microorganism in a gold (Au)-containing medium to synthesize gold nanoparticles in cells of the recombinant microorganism.

In accordance with a further aspect of the present invention, there is provided a method for removing radioactive iodine by using a recombinant microorganism having an enhanced radioactive iodine removal ability, the method including: (a) culturing the recombinant microorganism in a gold (Au)-containing medium to synthesize gold nanoparticles in cells of the recombinant microorganism; and (b) bringing the recombinant microorganism including the gold nanoparticles synthesized in the cells into contact with a solution containing radioactive iodine to bind the gold nanoparticles in the cells of the recombinant microorganism and the radioactive iodine, thereby removing the radioactive iodine.

DESCRIPTION OF DRAWINGS

The above and other objects, features and other advantages of the present invention will be more clearly understood from the following detailed description taken in conjunction with the accompanying drawings, in which.

BEST MODE

Unless defined otherwise, technical and scientific terms used herein have the same meaning as is commonly understood by one of ordinary skill in the art to which the present invention pertains. Generally, the nomenclature used herein is well known in the art and commonly used.

According to the present invention, it was confirmed that, when a gene encoding metallothionein or phytochelatin synthase, which is a gold-adsorbing protein, was codon-optimized to be introduced into *Deinococcus radiodurans*, the resulting bacterium was cultured in a gold-containing medium, and then *Deinococcus radiodurans* including gold nanoparticles synthesized in cells thereof was brought into contact with radioactive iodine, the radioactive iodine was removed by being adsorbed into the cells of the microorganism.

Therefore, an embodiment of the present invention relates to a recombinant microorganism having an enhanced radioactive iodine removal ability in which a polynucleotide having a nucleotide sequence of SEQ ID NO: 1 is introduced into *Deinococcus radiodurans* ATCC13939.

In the present invention, the polynucleotide may encode metallothionein and may be derived from *Pseudomonas putida*, but the present invention is not limited thereto.

Another embodiment of the present invention relates to a recombinant microorganism having an enhanced radioactive iodine removal ability in which a polynucleotide having a nucleotide sequence of SEQ ID NO: 2 is introduced into *Deinococcus radiodurans* ATCC13939.

In the present invention, the polynucleotide may encode phytochelatin synthase and may be derived from *Arabidopsis thaliana*, but the present invention is not limited thereto.

The polynucleotide of the present invention may be substituted with a codon having a high expression frequency in a host cell. As used herein, the expression "substituted with a codon having a high expression frequency in a host cell" or "codon-optimized" refers to a state of being substituted with codons having high preference, which are present between codons instructing amino acids according to a host when DNA in a host cell is transcribed and translated into proteins, thereby increasing the expression efficiency of amino acids or a protein encoded by nucleic acids thereof.

The genome of *Deinococcus radiodurans* of the present invention has a high G-C content, and thus genes encoding two types of proteins derived from *Pseudomonas* and *Arabidopsis* were codon-optimized in a high G-C version to be satisfactorily expressed in *Deinococcus radiodurans*.

In the present invention, the polynucleotide represented by a nucleotide sequence of SEQ ID NO: 1 or 2 may be codon-optimized for *Deinococcus radiodurans*.

As used herein, the term "polynucleotide" refers to an original gene or a variant thereof, or an encoding sequence of an original gene or a variant thereof.

The polynucleotide is operably linked to other nucleic acid sequences when placed in a functional relationship. The polynucleotide may be a polynucleotide and regulatory sequence(s) linked in such a way that a suitable molecule (e.g., a transcriptional activator protein) is capable of expressing the polynucleotide when binding to the regulatory sequence(s). For example, a nucleic acid for a pre-sequence or secretory leader is operably linked to a nucleic acid for the polypeptide when expressed as whole protein participating in the secretion of the polypeptide; a promoter or enhancer is operably linked to an encoding sequence when it affects the transcription of sequences; a ribosome binding site is operably linked to an encoding sequence when it affects the transcription of sequences; or a ribosome binding site is operably linked to an encoding sequence when positioned to facilitate translation. Generally, the expression "operably linked" refers to a state of being in contact with the linked nucleic acid sequence, and being in contact and present within a reading frame in the case of a secretory reader. However, the enhancer need not be in contact. The linkage of these sequences is carried out by ligation (linkage) at convenient restriction enzyme sites. When such a site does not exist, a synthetic oligonucleotide adapter or a linker according to a general method is used.

In an exemplary embodiment, the polynucleotide sequence is contained within a plasmid. In other exemplary embodiments, the polynucleotide sequence is incorporated into the genome of a host cell.

In the present invention, a recombinant vector including the polynucleotide may be introduced, and the recombinant vector may include a promoter for expressing the polynucleotide.

Figure 1:
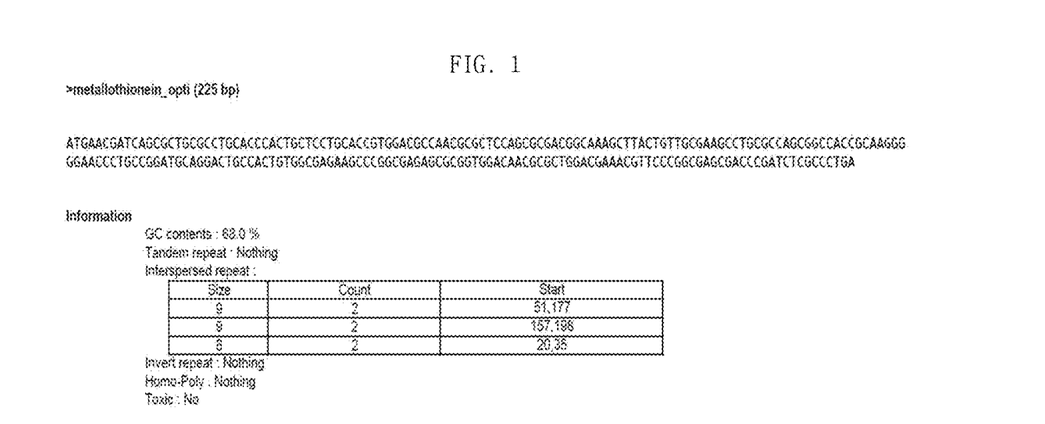
FIG. 1 shows a genetic base sequence in which the expression of a metallothionein protein of the *Pseudomonas putida* KT2440 strain was optimized for *Deinococcus radiodurans*.
Figure 2:
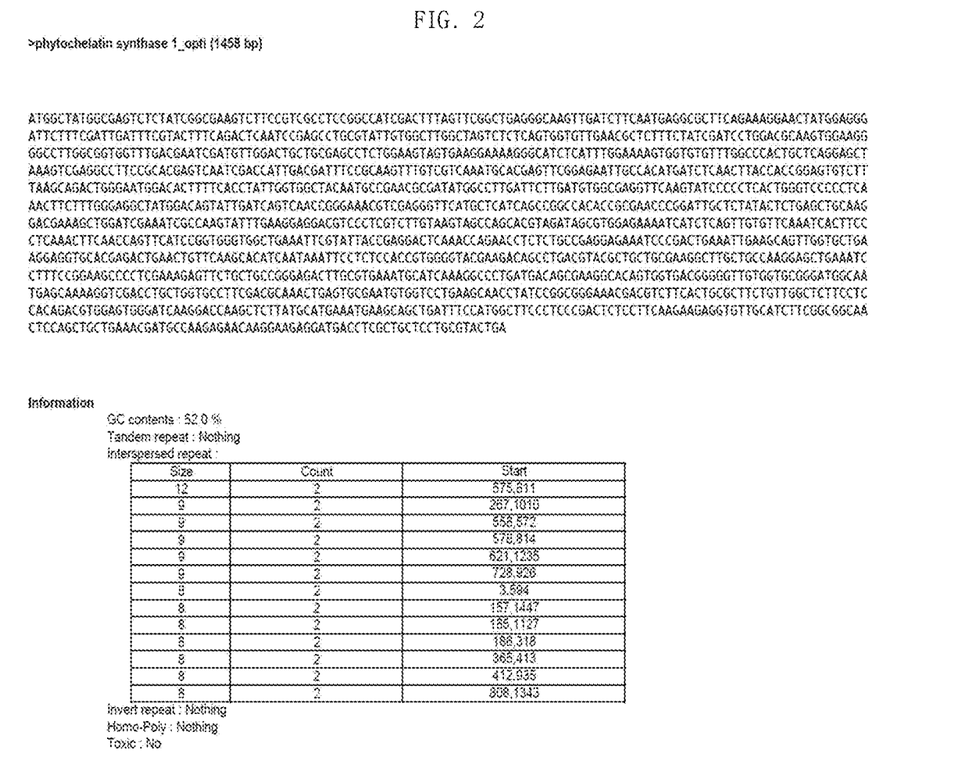
FIG. 2 shows a genetic base sequence in which the expression of the phytochelatin synthase protein of *Arabidopsis thaliana* col. was optimized for *Deinococcus radiodurans*.
Figure 3:
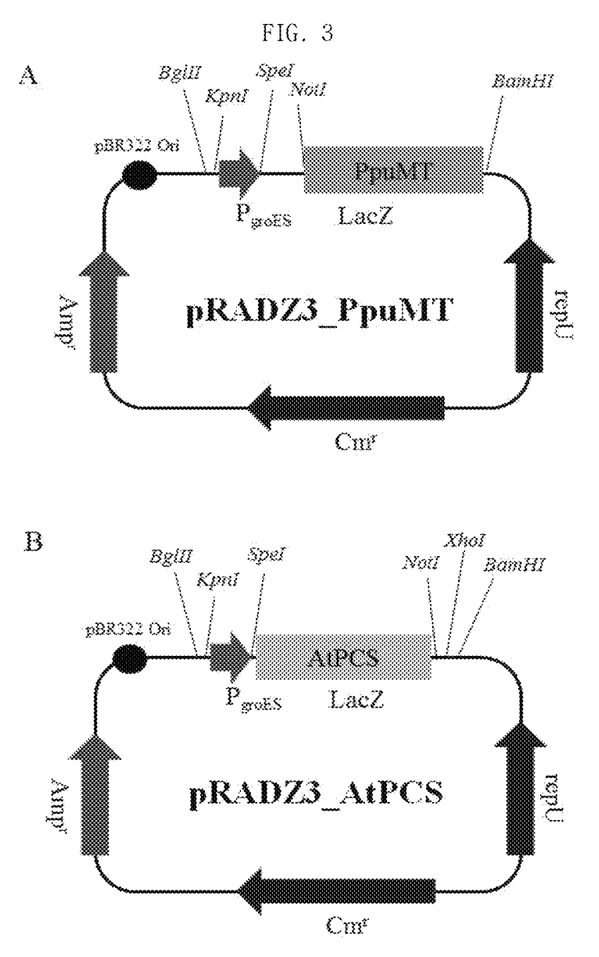
FIG. 3 shows the introduction of a gene encoding metallothionein (see FIG. 3A) and a gene encoding phytochelatin synthase (see FIG. 3B) that is codon-synthesized for *Deinococcus radiodurans*, into an expression vector.

In the present invention, an expression vector containing a gene encoding metallothionein of SEQ ID NO: 1 may be pRADZ3-PpuMT having a cleavage map illustrated in FIG. 3A, and an expression vector including a gene encoding phytochelatin synthase of SEQ ID: 2 may be pRADZ3-AtPCS having a cleavage map illustrated in FIG. 3B.

In the present invention, the vector means a DNA construct containing a DNA sequence operably linked to a suitable regulatory sequence capable of expressing DNA in an appropriate host. The vector may be a plasmid, a phage particle, or simply a latent genomic insert. When the vector is transformed into an appropriate host, the vector may be self-replicable or function regardless of a host genome, or may be integrated with the host genome in some cases. A plasmid is the most common type of vector, and thus the terms "plasmid" and "vector" are used interchangeably in the present specification. For the purpose of the present invention, a plasmid vector may be used. A typical plasmid vector that may be used for the purpose of the present invention has a structure including: (a) a replication origin enabling efficient replication such that hundreds of plasmid vectors are included in a host cell; (b) an antibiotic-resistance gene enabling a host cell transformed with a plasmid vector to be selected; and (c) a restriction enzyme cleavage site into which a foreign DNA fragment is capable of being inserted. Even though a suitable restriction enzyme cleavage site is not present, a vector and foreign DNA may be easily ligated using a synthetic oligonucleotide adapter or a linker according to a general method.

After ligation, the vector has to be transformed into an appropriate host cell. Transformation can be readily achieved using a calcium chloride method described in section 1.82 of *Sambrook*, et al., Supra. Alternatively, electroporation (Neumann, et al., *EMBO J.*, 1: 841, 1982) may be used to transform such cells.

As is well known in the art, to increase the expression level of a transfected gene in a host cell, the corresponding gene must be operably linked to a transcriptional and translational expression regulatory sequence that functions within the selected expression host. Preferably, the expression regulatory sequence and the corresponding gene are included within a recombinant vector containing a bacterial selection marker and a replication origin.

According to another embodiment of the present invention, there is provided a host cell transformed by the above-described recombinant vector. As used herein, the term "transformation" refers to the introduction of DNA into a host such that the DNA is replicable as an extrachromosomal factor or by chromosomal integration.

In the present invention, the host cell is preferably *Escherichia coli* or *Deinococcus radiodurans*, more preferably *Deinococcus radioresus* ATCC13939, but the present invention is not limited thereto.

In the present invention, the recombinant microorganism having an enhanced radioactive iodine removal activity may have the ability to synthesize gold nanoparticles in cells of the recombinant microorganism.

According to another embodiment of the present invention, there is provided a method of preparing gold nanoparticles by using a recombinant microorganism having an enhanced radioactive iodine removal ability, the method including culturing the recombinant microorganism in a gold (Au)-containing medium to synthesize gold nanoparticles in cells of the recombinant microorganism.

According to another embodiment of the present invention, there is provided a method for removing radioactive iodine by using a recombinant microorganism having an enhanced radioactive iodine removal ability, the method including: (a) culturing the recombinant microorganism in a gold (Au)-containing medium to synthesize gold nanoparticles in cells of the recombinant microorganism; and (b) bringing the recombinant microorganism including the gold nanoparticles synthesized in the cells into contact with a solution containing radioactive iodine to bind the gold nanoparticles in the cells of the recombinant microorganism and the radioactive iodine, thereby removing the radioactive iodine.

In the present invention, the type of the Au is not particularly limited, but the Au may be in the form of, for example, gold particles having an average particle diameter of 1 nm to 1 μm, preferably 10 nm to 100 nm, but the present invention is not limited thereto.

Meanwhile, in the present invention, iodine, which is a target material to be removed, may be present generally not only in the form of an iodine anion ($I^-$), iodine ($I_2$), an iodate ion ($IO_3^-$), or the like, but also in the form of an iodine cation ($I^+$), and thus it is not easy to remove iodine present in an aqueous solution or wastewater due to these various chemical forms.

As used herein, the term "iodine" refers to all types of iodine as described above and is intended to also include a mixture of various forms of iodine.

In the present invention, the solution containing iodine may be an aqueous solution, an organic solvent solution, or a combination thereof, but the present invention is not limited thereto.

In the present invention, the aqueous solution may be an acidic solution, a neutral solution, or a basic solution. The organic solvent is not particularly limited, but includes, for example, an organic solvent including ethanol, dimethylsulfoxide, or the like, or a mixture thereof.

In addition, the solution containing iodine may be in a liquid or gaseous state, and is not particularly limited.

Unless otherwise indicated, the practice of the present invention encompasses conventional techniques commonly used in biology, microbiology, and recombinant DNA in the art. Such techniques are well known to those of ordinary skill in the art and are described in numerous documents and references (For reference, e.g., Sambrook et al., "Molecular Cloning: A Laboratory Manual," Second Edition, Cold Spring Harbor, 1989; and Ausubel et al., "Current Protocols in Molecular Biology," 1987).

Unless otherwise defined herein, all technical and scientific terms have the same meaning as commonly understood in the art to which the present invention pertains. For example, [Singleton and Sainsbury, Dictionary of Microbiology and Molecular Biology, 2d Ed., John Wiley and Sons, NY (1994); and Hale and Marham, The Harper Collins Dictionary of Biology, Harper Perennial, NY (1991)] provides those skilled in the art with the general dictionary meanings of most terms used herein. Although any methods and materials similar or equivalent to those described herein have been found to be useful in the field of the present invention, suitable methods and techniques are described herein. Accordingly, the terms defined immediately below are more fully described when the present specification is referred to in its entirety.

EXAMPLES

Hereinafter, the present invention will be described in further detail with reference to the following examples. It will be obvious to those of ordinary skill in the art that these examples are provided only to explain the present invention in more detail and are not intended to limit the scope of the present invention in accordance with the essence of the present invention.

Example 1

Construction of Recombinant Vector Containing Codon-Optimized Gene 1-1: Construction of Expression Vector for Metallothionein A nucleotide sequence of SEQ ID NO: 1 was synthesized by codon-optimizing a gene (PpuMT) encoding metallothionein of *Pseudomonas putida* KT2440 for *Deinococcus radiodurans*. Then, polymerase chain reaction (PCR) was performed using primers of SEQ ID NO: 3 (GroMT_3) and SEQ ID NO: 4 (GroMT_4) using the codon-optimized PpuMT as a template.

```
(GroMT_3):
                                    SEQ ID NO: 3
ggcggccgttactagtggatatgaacgatcagcgctgcgc (GroMT_4):
                                    SEQ ID NO: 4
TATTGGATCCTCAGGGCGAGATCGGGTCGC
```

Meanwhile, the pRADZ3 plasmid was digested with NotI and BamHI restriction enzymes, and then pRADZ3 cut by gel extraction was isolated. At the same time, a GroES promoter was amplified by PCR using the pRADZ3 plasmid as a template and the primers of SEQ ID NO: 5 (GroMT_1) and SEQ ID NO: 6 (GroMT_2).

```
(GroMT_1):
                                    SEQ ID NO: 5
TATTGCGGCCGCTTGGAAGCACGTATTGTCGC (GroMT_2):
                                    SEQ ID NO: 6
gcgcagcgctgatcgttcatatccactagtaacggccgcc
```

Then, the PCR-amplified GroES promoter and the PpuMT gene were subjected to PCR using primers of SEQ ID NO: 5 (GroMT_1) and SEQ ID NO: 4 (GroMT_4) to link respective DNA fragments, thereby completing the construction of GroES promoter PpuMT.

The PCR fragment was cleaved with NotI and BamHI restriction enzymes, purified and ligated to the previously prepared pRADZ3 plasmid. Each ligation mixture was transformed into *E. coli* DH5a, selected in a LB/amp (50 μg/ml) medium, and then confirmed by PCR that each gene was correctly inserted (see FIG. 3A).

1-2: Construction of Expression Vector of Phytochelatin Synthase

The nucleotide sequence shown in SEQ ID NO: 2 was synthesized by codon-optimizing a gene (AtPCS) encoding phytochelatin synthase of *Arabidopsis thaliana* for *Deinococcus radiodurans*. Subsequently, PCR was performed using primers of SEQ ID NO: 7 (AtPCR_F) and SEQ ID NO: 8 (AtPCR_R) using the codon-optimized AtPCS as a template. The amplified PCR fragment was cleaved with speI and NotI and purified. At the same time, the pRADZ3 plasmid was digested with speI and NotI restriction enzymes and then pRADZ3 cut by gel extraction was isolated.

```
(AtPCR_F):
                                    SEQ ID NO: 7
GCCGCGACTAGTATGGCTATGGCGAGTCTCTATCG (AtPCR_R):
                                    SEQ ID NO: 8
TATATGCGGCCGCTCAGTACGCAGGAGCAGCGA
```

Then, the PCR fragment and pRADZ3 digested with speI and NotI were ligated. Each ligation mixture was transformed into *E. coli* DH5a, selected in a LB/amp (50 μg/ml) medium, and then confirmed by PCR that each gene was correctly inserted (see FIG. 3B).

Example 2

Production of *Deinococcus Radiodurans* Having Gold Nanoparticle Synthesis Ability 2-1: Production of Microorganisms for Radioactive Iodine Removal The pPADM3 plasmid constructed according to Example 1 into which PpuMT or AtPCS was inserted was transformed into *Deinococcus radiodurans* R1 ATCC13939, and *E. coli* was used as a control.

The transformed microorganism was pre-cultured in 5 ml of a liquid medium containing TGY (Tryptone 0.5%, glucose 0.1%, yeast extract 0.3%) and 3 μg/ml of chloramphenicol, 50 ml of fresh TGY was added to a 250 ml flask and subjected to dilution to a final O.D. of 0.1, and then the microorganism was cultured at 30° C. and 200 rpm up to O.D. 1. Thereafter, a gold (III) chloride hydrate solution was added to the culture solution to a final concentration of 1.25 mM, and further cultured for 16 hours (overnight) to synthesize gold nanoparticles in the cells of *Deinococcus radiodurans*.

The *Deinococcus radiodurans* culture solution, in which the synthesized gold nanoparticles were present in the cells, was transferred to a 50 ml conical tube, centrifuged at 4,000 rpm for 20 minutes, washed three times with 20 ml of sterilized distilled water and finally re-suspended in 5 ml of sterilized distilled water, thereby completing the preparation of a stain to be used for removing radioactive iodine.

2-2: Confirmation of Synthesis of Gold Nanoparticles of *Deinococcus Radiodurans*

The *Deinococcus radiodurans* prepared according to Example 2-1 was cultured in a gold-free medium or a gold-containing medium, and then analyzed using a dark-field microscope (Olympus BX-43) at a magnification of 60× and observed using a transmission electron microscope (TEM).

Figure 4:
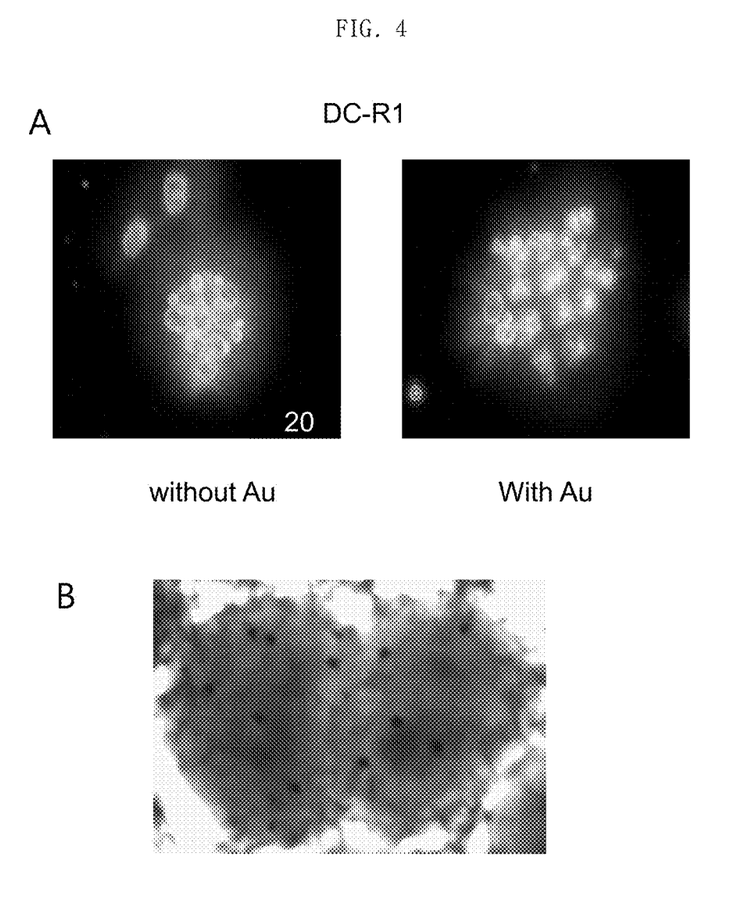
FIG. 4 is a set of dark-field microscope and transmission electron microscope images showing observation results of the synthesis of gold nanoparticles in *Deinococcus radiodurans* cells.

As a result, it was confirmed that gold nanoparticles were synthesized in the cells of *Deinococcus radiodurans* cultured in the gold-containing medium (see FIGS. 4A and 4B).

Figure 5:
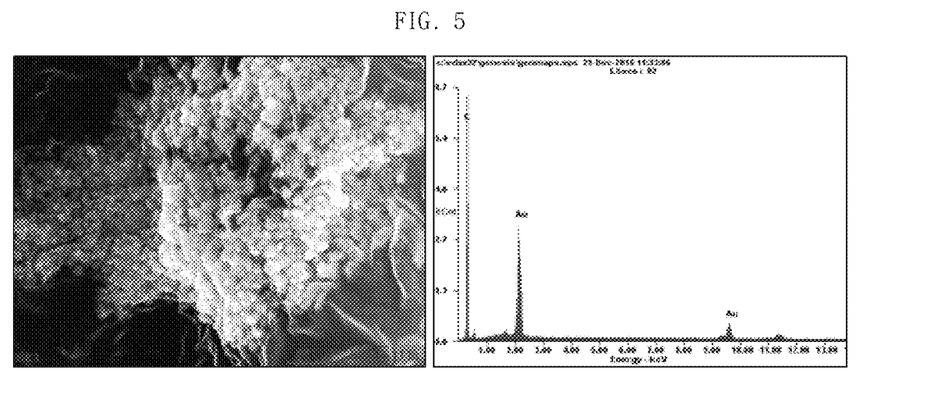
FIG. 5 shows observation results of gold nanoparticles synthesized in *Deinococcus radiodurans*, which were obtained by a field-emission-type scanning electron microscope, and SEM-energy dispersive X-ray spectroscopy results.

Next, the *Deinococcus radiodurans* centrifuged and washed, and bead-beating was performed thereon at 6 m/s for 1 minute using a FastPrep-24 instrument (MP Biomedical, Korea) to crush the resulting product. The gold nanoparticles were purified from the crushed sample using a 0.22 μm syringe filter, and the purified gold nanoparticles were dropped onto a carbon tape and dried for 10 minutes. The dried sample was coated with platinum using an ion sputter, and gold nanoparticles were observed with an FEI Verios 460L Field-Emission-type Scanning Electron Microscope (FE-SEM). The basic composition of the gold nanoparticles was subjected to SEM-energy dispersive X-ray (EDX) analysis and EDX spectroscopy as illustrated in FIG. 5.

Example 3

Removal of Radioactive Iodine Using *Deinococcus Radiodurans*

Figure 6:
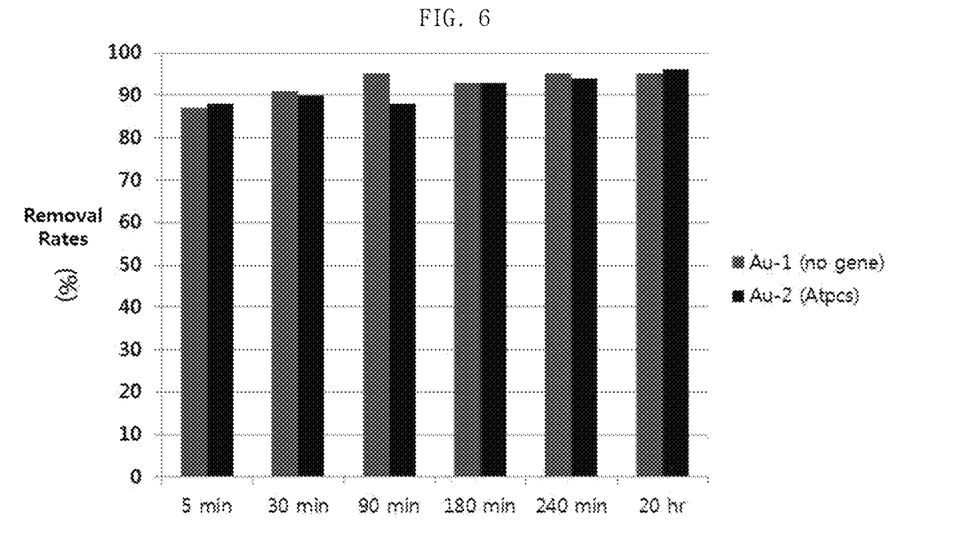
FIG. 6 is a graph showing NaI removal rates of *Deinococcus radiodurans* R1 ATCC13939 having no gold nanoparticle synthesis ability as a control and radioactivity-resistant *Deinococcus radiodurans* R1 into which a gene encoding phytochelatin synthase was introduced, wherein the *Deinococcus radiodurans* R1 was induced to synthesize gold nanoparticles.
Figure 7:
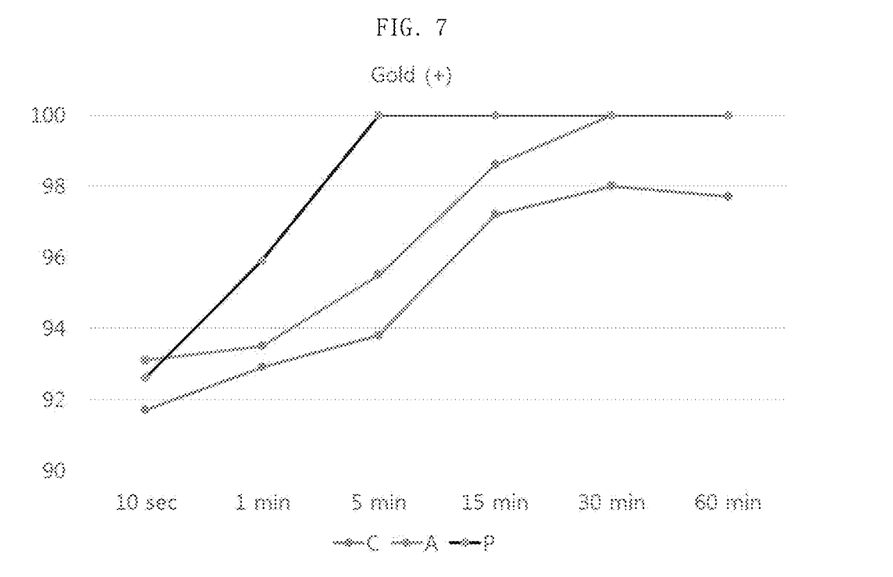
FIG. 7 is a graph showing NaI removal rates of radioactivity-resistant *Deinococcus radiodurans* R1 into which a gene encoding codon-optimized metallothionein or phytochelatin synthase was introduced, wherein the microorganism was induced to synthesize gold nanoparticles (C: control, A: AtPCS, and P: PpuMT)

3-1: *Deinococcus Radiodurans* Having Gold Nanoparticle Synthesis Ability 1 ml of *Deinococcus radiodurans* prepared according to Example 2 into which AtPCS or PpuMT was introduced was added to 5 ml of DW containing 100 µCi [$^{125}$I] NaI under the condition of 1.25 mM Au$^{3+}$ and incubated at room temperature, and iodine removal efficacy thereof was analyzed by Radio-TLC over time (See FIGS. 6 and 7). As a control, iodine removal efficacy was analyzed using *E. coli* under the same conditions.

As a result, it was confirmed that *Deinococcus radiodurans* had a radioactive iodine removing ability even when AtPCS or PpuMT was not introduced thereinto (See FIG. 6).

Thus, enhanced radioactive iodine removal ability of the *Deinococcus radiodurans* into which the codon-optimized AtPCS or PpuMT was introduced was confirmed.

As a result, the PpuMT-introduced *Deinococcus radiodurans* exhibited a remarkably great radioactive iodine removal ability within one minute as compared with *Deinococcus radiodurans* without the ability to synthesize gold nanoparticles, and exhibited a radioactive iodine removal ability of nearly 100% in 5 minutes (see FIG. 7). From these results, it was confirmed that the PpuMT-introduced *Deinococcus radiodurans* exhibited a significantly high radioactive iodine removal efficiency, as compared to that of the AtPCS-introduced *Deinococcus radiodurans*, i.e., about 100% in 30 minutes and that of *Deinococcus radiodurans* having no gold nanoparticle synthesis ability, i.e., about 98% in 30 minutes.

3-2: *E. coli* Having Gold Nanoparticle Synthesis Ability

Iodine removal efficacy of each of the AtPCS- or PpuMT-introduced *E. coli* prepared according to Example 2 and *E. coli* into which both AtPCS and PpuMT were introduced, as a control was analyzed under the same condition as that used in Example 3-1.

As a result, it was confirmed that, unlike *Deinococcus radiodurans*, *E. coli* had no radioactive iodine removal ability unless AtPCS or PpuMT was introduced (see Table 1).

TABLE 1

|  | Au-1 (PpuMT) | Control-1 | Au-2 (AtPCS + PpuMT) | Control-2 |
|---|---|---|---|---|
| 15 min | 68 | 0 | 78 | 0 |
| 150 min | 91 | 0 | 95 | 0 |
| 15 h | 99 | 0 | 99 | 0 |

Figure 8:
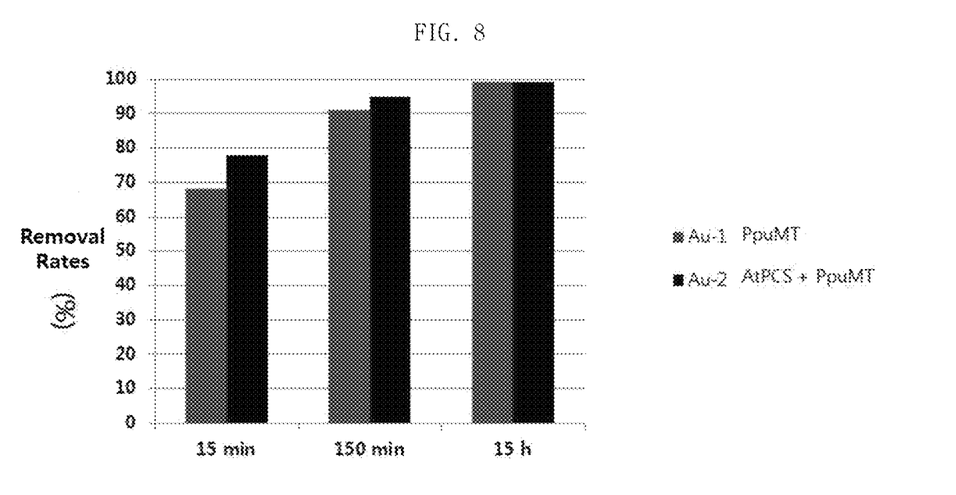
FIG. 8 is a graph showing NaI removal rates of *E. coli* into which a gene encoding codon-optimized metallothionein was introduced or both a gene encoding metallothionein and a gene encoding phytochelatin synthase were introduced, wherein the *E. coli* was induced to synthesize gold nanoparticles.

In addition, it was confirmed that *E. coli* into which PpuMT, which had exhibited excellent iodine removal in the *Deinococcus radiodurans* of Example 3-1, was introduced exhibited a radioactive iodine removal efficiency of 68% in 15 minutes and 99% in 15 hours (see FIG. 8).

Therefore, *E. coli* having a further enhanced gold nanoparticle synthesis ability was prepared by introducing both AtPCS and PpuMT thereinto, and the radioactive iodine removal ability thereof was examined.

As a result, it was confirmed that the above case exhibited an enhanced radioactive iodine removal ability as compared to the case of *E-coli* into which only PpuMT was introduced, while exhibiting a significantly reduced radioactive iodine removal efficiency as compared to the case of *Deinococcus radiodurans* into which AtPCS or PpuMT was introduced.

INDUSTRIAL APPLICABILITY

A recombinant microorganism having an enhanced radioactive iodine removal ability according to the present invention can selectively remove radioactive iodine present in various types of solutions at a high efficiency of 99% or higher, and thus may be very effective in removing radioactive iodine generated in large-scale hospitals, industries, nuclear facility accidents, and the like.

While the present invention has been particularly shown and described with reference to specific embodiments thereof, it will be obvious to those of ordinary skill in the art that these are merely exemplary embodiments and are not intended to limit the scope of the present invention. Therefore, the true scope of the present invention should be defined by the appended claims and equivalents thereto.

The invention claimed is:

1. A recombinant microorganism having an enhanced radioactive iodine removal ability in which a polynucleotide comprising the nucleotide sequence of SEQ ID NO: 1 or SEQ ID NO: 2 has been introduced into *Deinococcus radiodurans* ATCC13939.

2. The recombinant microorganism according to claim 1, wherein the polynucleotide comprising the nucleotide sequence of SEQ ID NO: 1 encodes metallothionein and is derived from *Pseudomonas putida*.

3. The recombinant microorganism according to claim 1, wherein the polynucleotide comprising the nucleotide sequence of SEQ ID NO: 2 encodes phytochelatin synthase and is derived from *Arabidopsis thaliana*.

4. The recombinant microorganism of claim 1, wherein a recombinant vector comprising the polynucleotide is introduced.

5. The recombinant microorganism of claim 1, wherein the recombinant microorganism has a gold nanoparticle synthesis ability in cells of the recombinant microorganism.

6. A method for removing radioactive iodine by using a recombinant microorganism having a gold nanoparticle synthesis ability and an enhanced radioactive iodine removal ability, the method comprising:

(a) culturing the recombinant microorganism of claim 1 in a gold (Au)-containing medium to synthesize gold nanoparticles in cells of the recombinant microorganism; and (b) bringing the recombinant microorganism comprising the gold nanoparticles synthesized in the cells into contact with a solution containing radioactive iodine to bind the gold nanoparticles in the cells of the recombinant microorganism and the radioactive iodine, thereby removing the radioactive iodine.

7. The method according to claim 6, wherein the gold is in the form of particles having an average particle diameter of 1 nm to 1 µm.

8. The method according to claim 6, wherein the solution is an aqueous solution, an organic solvent solution, or a combination thereof.

9. The method according to claim 8, wherein the aqueous solution is an acidic solution, a neutral solution, or a basic solution.

10. The method according to claim 6, wherein the iodine comprises any one or more selected from the group consisting of an iodine anion ($I^-$), an iodine cation ($I^+$), an iodate ion ($IO_3^-$), and iodine ($I_2$).

* * * * *